United States Patent [19]

Nicolaides et al.

[11] 4,101,537

[45] Jul. 18, 1978

[54] OCTAPEPTIDES AND METHODS FOR THEIR PRODUCTION

[75] Inventors: Ernest D. Nicolaides; Francis John Tinney, both of Ann Arbor, Mich.

[73] Assignee: Parke, Davis & Company, Detroit, Mich.

[21] Appl. No.: 785,393

[22] Filed: Apr. 7, 1977

[51] Int. Cl.$^2$ .................... C07C 103/52; A61K 37/00
[52] U.S. Cl. .................. 260/112.5 LH; 260/112.5 R; 424/177
[58] Field of Search .............. 260/112.5 R, 112.5 LH; 424/177

[56] References Cited

FOREIGN PATENT DOCUMENTS 2,348,221  4/1974  Fed. Rep. of Germany .... 260/112.5 R

*Primary Examiner*—Delbert R. Phillips
*Attorney, Agent, or Firm*—Stephen Raines; David B. Ehrlinger; Frank S. Chow

[57] ABSTRACT

New octapeptides having the formula X-$R^1$-Trp-Ser(benzyl)-Tyr(benzyl)-$R^2$-Leu-Arg(R)-Pro-$R^3$-Y wherein X is a protective group, R is hydrogen or a protective group, $R^1$ is a single bond, Gln, D-Leu or D-Val, $R^2$ is D-Phe or D-Ala, $R^3$ is a single bond or Gly and Y is lower alkoxy, amino, lower alkylamino or di(lower alkyl)amino.

11 Claims, No Drawings

OCTAPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new N-protected octapeptides that are represented by the formula

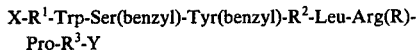

X-R¹-Trp-Ser(benzyl)-Tyr(benzyl)-R²-Leu-Arg(R)-Pro-R³-Y    I wherein X is a protective group, preferably t-butoxycarbonyl or benzyloxycarbonyl, R is hydrogen or a protective group, preferably nitro or (4-methylphenyl)sulfonyl R¹ is a single bond, Gln, D-Leu or D-Val, R² is D-Phe or D-Ala, R³ is a single bond or Gly and Y is lower alkoxy, amino, lower alkylamino or di(lower alkyl)amino and wherein R is hydrogen, acid addition salts thereof.

The preferred compounds of formula I are those wherein X is t-butoxycarbonyl or benzyloxycarbonyl, R is hydrogen, nitro or (4-methylphenyl)sulfonyl and Y is methoxy, amino or ethylamino.

In formula I, the conventional symbols for amino acid residues of peptide compounds linked thereto are used and each is intended to have the following meaning: Pro, D-prolyl or L-prolyl; Tyr(benzyl), D-tyrosyl(benzyl) or L-tyrosyl(benzyl); Ser(benzyl), D-seryl(benzyl) or L-seryl(benzyl); D-Phe, D-phenylalanyl; Leu, L-leucyl or D-leucyl; Arg, D-arginyl or L-arginyl; D-Ala, D-alanyl; Trp, D-tryptophyl or L-tryptophyl; D-Val, D-Valyl; D-Leu, D-leucyl; D-Gln, D-glutaminyl and Gly, glycyl. In addition, the term "lower alkyl" is intended to mean a straight, branched or cyclic hydrocarbon moiety of up to six carbon atoms, such as methyl, ethyl, isopropyl and cyclopropyl and "lower alkoxy" is intended to mean an alkoxy group having a straight, branched or cyclic hydrocarbon moiety of up to six carbon atoms, such as methoxy, ethoxy and isopropoxy. A protective group as defined for X is intended to mean a group usually employed in the area of peptides for protecting an amino function, such groups are disclosed in the following texts which are incorporated by reference: E. Schroder and K. Lubke, "The Peptides", Vol. I, Chapter 1., Academic Press, 1966 and J. Meienhofer in "Hormonal Proteins and Peptides", Vol. II, p. 227., Academic Press, 1973. A protective group as defined for R is intended to mean a group usually employed for protecting the N^G-guanidino moiety of the amino acid arginine. Such groups are also disclosed in the above cited references. These symbols and terms will also be used in the formulae that follow for other compounds and each such symbol or term should be understood to have the meaning given above.

In accordance with this invention, compounds of the formula I, wherein X, R¹, R² and R³ are as previously defined and R is a protective group and Y is lower alkoxy, are produced by removing a protected octapeptide from a resin complex of the following structure X-R¹-Trp-Ser(benzyl)-Tyr(benzyl)-R²-Leu-Arg(R⁴)-Pro-R³-resin    II

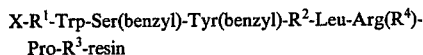

wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected octapeptide through a methyleneoxy bridge wherein the methylene group is attached to the polymeric portion of the resin and the oxygen atom is attached to the protected octapeptide and X, R¹, R² and R³ are as previously defined and R⁴ is a protective group; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° C. to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein Y is amino, lower alkylamino or di(lower alkyl)amino may be prepared by reacting compounds of the formula II wherein X, R¹, R² and R³ are as previously defined and R is a protective group, with ammonia, lower alkylamine or di(lower alkyl)amine.

The resin complex is suspended in a solvent, such as methanol, ethanol, dimethylformamide, etc., at a temperature of from about 0° C. to 50° C. for periods of from 12 hours to 10 days. When employing less reactive amines, the preferred solvent is dimethylformamide.

Certain of the complex resins of the formula II are prepared by coupling a protected amino acid of the formula

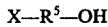

X—R⁵—OH    III with complex resins of the formula

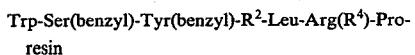

Trp-Ser(benzyl)-Tyr(benzyl)-R²-Leu-Arg(R⁴)-Pro-resin    IV wherein X and R² are as previously defined in formula I, R⁵ is Glu, D-Leu or D-Val and R⁴ is a protective group, in an organic solvent, such as dichloromethane with the aid of dicyclohexylcarbodiimide. The three reactants may be used in about equimolar quantities, but excess amounts of the protected amino acid and dicyclohexylcarbodiimide are sometimes advantageous. The reaction is generally conducted at about room temperature for a period of from about fifteen minutes to about 20 hours.

The complex resins of the formula IV are prepared by treating complex resins of the formula

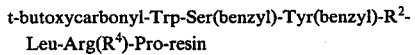

t-butoxycarbonyl-Trp-Ser(benzyl)-Tyr(benzyl)-R²-Leu-Arg(R⁴)-Pro-resin    V wherein R² and R⁴ are as previously defined in formula I and II, respectively with a large excess of trifluoroacetic acid utilizing dichloromethane as the solvent at temperatures of from 20° C. to 30° C. for about 10 minutes followed by neutralization of the trifluoroacetic acid salt with a base such as triethylamine.

The complex resins of the formula V and certain compounds of the invention are prepared by coupling t-butoxycarbonyl-Trp-OH to complex resins of the formula Ser(benzyl)-Tyr(benzyl)-R$^2$-Leu-Arg(R$^4$)-Pro-R$^3$-
resin        VI wherein R$^2$ and R$^3$ are as previously defined in formula I and R$^4$ in formula II, respectively using the reaction procedure described for the preparation of compounds of the formula II.

The complex resins of the formula VI are prepared by treating the complex resins of the formula t-butoxycarbonyl-Ser(benzyl)-Tyr(benzyl)-R$^2$-Leu-
Arg(R$^4$)-Pro-R$^3$-resin        VII wherein R$^2$ and R$^3$ are as previously defined in formula I and R$^4$ as previously defined in formula II, with trifluoroacetic acid using the reaction procedure for the preparation of compounds of the formula IV.

The complex resins of the formula VII are prepared by coupling t-butoxycarbonyl-Ser(benzyl)-OH to complex resins of the formula Tyr(benzyl)-R$^2$-Leu-Arg(R$^4$)-Pro-R$^3$-resin        VIII wherein R$^2$ and R$^3$ are as previously defined in formula I and R$^4$ is as previously defined in formula II, according to the procedure used for the preparation of compounds of formula II.

The complex resins of the formula VIII are prepared by treating the complex resins of the formula t-butoxycarbonyl-Tyr(benzyl)-R$^2$-Leu-Arg(R$^4$)-Pro-
R$^3$-resin        IX wherein R$^2$ and R$^3$ are previously defined in formula I and R$^4$ is as previously defined in formula II, with trifluoroacetic acid using the reaction procedure for the preparation of compounds of the formula IV.

The complex resins of the formula IX are prepared by coupling t-butoxycarbonyl-Tyr(benzyl)-OH to complex resins of the formula R$^2$-Leu-Arg(R$^4$)-Pro-R$^3$-resin        X wherein R$^2$ and R$^3$ are as defined in formula I and R$^4$ is as previously defined in formula II, according to the procedure used for the preparation of compounds of formula II.

The complex resins of the formula X are prepared by treating the complex resins of the formula t-butoxycarbonyl-R$^2$-Leu-Arg(R$^4$)-Pro-R$^3$-resin        XI wherein R$^2$ and R$^3$ are as defined in formula I and R$^4$ is as defined in formula II, with trifluoroacetic acid using the reaction procedure for the preparation of compounds of the formula IV.

Certain of the complex resins of formula XI are prepared by coupling t-butoxycarbonyl-R$^2$-OH to complex resins of the formula Leu-Arg(R$^4$)-Pro-R$^3$-resin        XII wherein R$^2$ and R$^3$ are as defined in formula I and R$^4$ is as defined in formula IV, according to the procedure used for the preparation of compounds of formula II.

The complex resins of the formula XII are prepared by treating the complex resins of the formula t-butoxycarbonyl-Leu-Arg(R$^4$)-Pro-R$^3$-resin        XIII wherein R$^3$ is as defined in formula I and R$^4$ is as defined in formula IV, with trifluoroacetic acid using the reaction procedure for the preparation of compounds of formula IV.

The complex resins of formula XIII are prepared by coupling t-butoxycarbonyl-Leu-OH to a complex resin of the formula Arg(R$^4$)-Pro-R$^3$-resin        XIV wherein R$^3$ is as defined in formula I and R$^4$ is as defined in formula IV, according to the procedure used for the preparation of compounds of formula II.

The complex resins of the formula XIV are prepared by treating complex resins of the formula t-butoxycarbonyl-Arg(R$^4$)-Pro-R$^3$-resin        XV wherein R$^3$ is as defined in formula I and R$^4$ is as defined in formula IV, with trifluoroacetic acid using the reaction procedure for the preparation of compounds of formula IV.

The complex resins of the formula XV are prepared by coupling t-butoxycarbonyl-Arg(R$^4$)-OH to a complex resin of the formula Pro-R$^3$-resin        XVI wherein R$^3$ is as defined in formula I and R$^4$ is as defined in formula IV, according to the procedure used for the preparation of compounds of formula II.

The complex resins of the formula XVI are prepared by treating complex resins of the formula t-butoxycarbonyl-Pro-R$^3$-resin        XVII wherein R$^3$ is as defined in formula I, with trifluoroacetic acid using the reaction procedure for the preparation of compounds of formula IV.

The complex resins of the formula XVII are prepared by coupling t-butoxycarbonyl-Pro-OH to a complex resin of the formula R$^3$-resin        XVIII wherein R$^3$ is as defined in formula I, according to the procedure used for the preparation of compounds of the formula II.

The complex resins of the formula XVIII are prepared by treating complex resins of the formula t-butoxycarbonyl-R³-resin                XIX wherein R³ is as defined in formula I, with trifluoroacetic acid using the reaction procedure for the preparation of compounds of formula IV.

In accordance with this invention, compounds of the formula I, wherein X, R, R¹, R² and R³ are as described in formula I and Y is amino, lower alkylamino or di(-lower alkyl)amino are prepared by reacting a compound of the formula I wherein Y is lower alkoxy, preferably methoxy, with ammonia, lower alkylamine or di(lower alkylamine).

The reactions are conducted at temperatures of from about 5° to 100° C. for from three hours to four days, preferably about room temperature. Generally, a large excess of amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

Compounds of the formula I wherein X, R¹, R² and R³ are as described in formula I, R is a protective group and Y is amino, lower alkylamino or di(lower alkyl)amino are prepared by coupling a compound of the formula X-Ser(benzyl)-Tyr(benzyl)-Phe-Leu-Arg(R⁴)-Pro-Gly-OH                XX wherein R⁴ is a protective group, with ammonia, a lower alkylamine or a di(lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° to 50° C., preferably room temperature for periods of from ten hours to five days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula XX are prepared by the hydrolysis of a compound of formula I wherein X, R¹, R² and R³ are as defined in formula I, R⁴ is a protective group and Y is lower alkoxy. The reaction is conducted at temperatures of from 20° to 30° C. using about 0.5 ml. of two normal aqueous sodium hydroxide solution and 10 ml. of solvent, usually water or an alcohol such as methanol, for each millimole of ester. The compound of formula XX is isolated after acidification with aqueous citric acid.

Also, in accordance with this invention, compounds of the formula I wherein X, Y, R¹, R² and R³ are as described in formula I and R is hydrogen are produced by reacting an azide, represented by the formula X-R¹-Trp-Ser(benzyl)-Tyr(benzyl)-R²-N₃                XXI with a compound of the formula Leu-Arg-Pro-R₃-Y                XXII in a non-reactive solvent medium, preferably dimethylformamide or a dimethylformamide-tetrahydrofuran mixture wherein X, Y, R¹, R² and R³ are as previously defined.

The azide of the formula XXI is prepared and used in situ, while the compound of formula XXII is used with the Arg group in the form of an acid-addition salt of a strong acid, such as the hydrochloride or trifluoroacetate. The two components, XXI and XXII are generally reacted in approximately equimolar amounts at temperatures of from about −30° C. to about 30° C. for from sixteen to fifty hours, although temperatures of from 30° to 50° C. may be used with a shortened reaction period.

The compounds of formula I wherein R is hydrogen are preferably isolated in the form of an acid-addition salt but may if desired be isolated in the form of a free base.

The peptide azide compounds of the formula XXI that are used as a reactant in the foregoing process are normally prepared in situ by reacting a peptide hydrazide compound represented by the formula X-R¹-Trp-Ser(benzyl)-Tyr(benzyl)-R²-NHNH₂                XXIII wherein X, R¹ and R² are as previously described in formula I, with a lower alkyl nitrite, preferably isoamyl nitrite in the presence of an acid in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula XXIII. The preparation of the azide is carried out at a temperature between −60° C. and 10° C. Following the in situ formation of the azide of formula XXI and prior to the further reaction of the peptide azide with the compound of formula XXII to form the octapeptide of the formula I wherein R is hydrogen, a tertiary amine such as triethylamine is added to the reaction mixture to neutralize the acid used.

The peptide hydrazide compounds of formula XXIII above are prepared by various methods. Certain of these compounds can exist in the form of acid-addition salts, such as the hydrochloride salt, sulfate salt, acetate salt, citrate salt, trifluoroacetate salt, etc. The hydrazides of the formula XXIII are prepared by reacting an ester of the formula X-R¹-Trp-Ser(benzyl)-Tyr(benzyl)-R²-O-lower alkyl                XXIV wherein X, R¹ and R² are as previously defined in formula I and lower alkyl is preferably methyl, with excess hydrazine (1:1.1 to 100) preferably in the form of its hydrate, in an organic solvent, such as dimethylformamide, methanol, ethanol, etc. The reaction is generally carried out at room temperature, although temperatures of from 5° to 100° C. may be employed for periods of from about 30 minutes to about 200 hours, preferably about 72 hours.

The compounds of formula XXIV are prepared by generally known procedures as shown in the examples.

The compounds of formula XXII are also prepared by generally known procedures as shown in the examples.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

The acid addition salts of this invention wherein R is hydrogen are exemplified by the following salts, hydrochloride, hydrobromide, sulfate, acetate, pamoate, citrate, etc. Of the salts of this type, pharmaceutically acceptable salts are preferred.

Octapeptides of this invention were screened for LRF antagonist activity in vitro using rat anterior pituitary cell cultures as described by Vale et. al. [Endocrinology, 91, 562 (1972)]. The inhibition of LRF (luteinizing hormone releasing factor) induced luteinizing hormone (LH) release into the culture medium is the endpoint in this in vitro bioassay.

Following are the results of the above tests on certain preferred compounds.

ACTIVITY TABLE FOR IN VITRO TEST
IN RAT ANTERIOR PITUITARY
CELL CULTURES

| Compound | Molar Conc. | LH Value ng/ml. | % LH Release Inhibition |
|---|---|---|---|
| $N^\alpha$-t-Butoxycarbonyl-L-tryptophyl--O-benzyl-L-seryl-O-benzyl-L--tyrosyl-D-phenylalanyl-L-leucyl--$N^G$-nitro-L-arginyl-L-prolyl-glycine methyl ester | $2\times10^{-7}$ | 9.62 | 118 |
| | $1\times10^{-7}$ | 12.38 | 107 |
| | $6\times10^{-8}$ | 12.80 | 105 |
| | $3.5\times10^{-8}$ | 18.11 | 85 |
| | $2\times10^{-8}$ | 26.23 | 53 |
| | $3.5\times10^{-10}$ | 47.18 | |
| LRF Control | $3.5\times10^{-10}$ | 63.90 | |
| Saline Control | | 24.72 | |
| $N^\alpha$-t-Butoxycarbonyl-L-tryptophyl--O-benzyl-L-seryl-O-benzyl-L--tyrosyl-D-phenylalanyl-L-leucyl--$N^G$-nitro-L-arginyl-L-prolyl-glycinamide | $6\times10^{-7}$ | 12.05 | 98 |
| | $6\times10^{-8}$ | 11.50 | 99 |
| | $1\times10^{-7}$ | 12.29 | 97 |
| | $2\times10^{-7}$ | 16.12 | 90 |
| | $3.5\times10^{-7}$ | 16.95 | 89 |
| LRF Control | $3.5\times10^{-10}$ | 64.13 | |
| Saline Control | | 10.79 | |
| | $6\times10^{-9}$ | 28.10 | 91 |
| | $3.5\times10^{-9}$ | 32.43 | 80 |
| | $2\times10^{-9}$ | 38.24 | 66 |
| | $1\times10^{-9}$ | 40.16 | 61 |
| | $6\times10^{-10}$ | 45.76 | 46 |
| | $3.5\times10^{-10}$ | 47.18 | 43 |
| $N^\alpha$-t-Butoxycarbonyl-L-tryptophyl--O-benzyl-L-seryl-O-benzyl-L--tyrosyl-D-phenylalanyl-L-leucyl--$N^G$-nitro-L-arginyl-L-prolyl-glycine N-ethylamide | $6\times10^{-7}$ | 11.99 | 98 |
| | $3.5\times10^{-7}$ | 15.10 | 92 |
| | $2\times10^{-7}$ | 12.13 | 98 |
| | $1\times10^{-7}$ | 15.45 | 91 |
| | $6\times10^{-8}$ | 15.60 | 91 |
| LRF Control | $3.5\times10^{-10}$ | 64.13 | |
| Saline Control | | 10.79 | |
| | $6\times10^{-8}$ | 10.12 | 116 |
| | $3.5\times10^{-8}$ | 13.92 | 101 |
| | $2\times10^{-8}$ | 20.36 | 76 |
| | $1\times10^{-8}$ | 22.86 | 66 |
| | $6\times10^{-9}$ | 26.04 | 54 |
| LRF Control | $3.5\times10^{-10}$ | 40.01 | |
| Saline Control | | 14.18 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511–512. Thus, the octapeptides of this invention are useful in controlling ovulation and in restricting fertility.

The invention is illustrated by the following examples.

EXAMPLE 1

$N^\alpha$-t-Butoxycarbonyl-L-tryptophyl-O-benzyl-L-seryl-O-benzyl-L-tyrosyl-D-phenylalanyl-L-leucyl-$N^G$-nitro-L-arginyl-L-prolyl-glycine resin 21 g., is treated with 300 ml. of methanol and 25 ml. of triethylamine at room temperature for three days. After filtration and evaporation, the crude product is an oil. Pure $N^\alpha$-t-butoxycarbonyl-L-tryptophyl-O-benzyl-L-seryl-O-benzyl-L-tyrosyl-D-phenylalanyl-L-leucyl-$N^G$-nitro-L-arginyl-L-prolyl-glycine methyl ester is obtained after two times precipitating the product from cooled isopropanol; 5 g.; m.p. 154°–156° C.

$N^\alpha$-t-Butoxycarbonyl-L-tryptophyl-O-benzyl-L-seryl-O-benzyl-L-tyrosyl-D-phenylalanyl-L-leucyl-$N^G$-nitro-L-arginyl-L-prolyl-glycine resin is prepared according to the General Procedure given below from 10 g. (9 mmol) of $N^\alpha$-t-butoxycarbonyl-glycine resin by successive coupling with 1.) 2 g. (9.3 mmol) of $N^\alpha$-t-butoxycarbonyl-L-proline and 2 g. (9.7 mmol) of dicyclohexylcarbodiimide, 2.) 3 g. (9.4 mmol) of $N^\alpha$-t-butoxycarbonyl-$N^G$-nitro-L-arginine and 2 g. of dicyclohexylcarbodiimide, 3.) 2.2 g. (9.5 mmol) of $N^\alpha$-t-butoxycarbonyl-L-leucine and 2 g. of dicyclohexylcarbodiimide, 4.) 2.6 g. (9.8 mmol) of $N^\alpha$-t-butoxycarbonyl-D-phenylalanine and 2.06 g. (10 mmol) of dicyclohexylcarbodiimide, 5.) 3.7 g. (10 mmol) of $N^\alpha$-t-butoxycarbonyl-O-benzyl-L-tyrosine and 2.06 g. of dicyclohexylcarbodiimide, 6.) 3.0 g. (9.9 mmol) of $N^\alpha$-t-butoxycarbonyl-O-benzyl-L-serine and 2.06 g. of dicyclohexylcarbodiimide and 7.) 3.0 g. (10.8 mmol) of $N^\alpha$-t-butoxycarbonyl-L-tryptophan and 2.06 g. of dicyclohexylcarbodiimide.

$N^\alpha$-t-Butoxycarbonyl glycine resin is obtained by refluxing 100 g. (0.116 mol) of 1% chloromethylated resin, 22.3 g. (0.13 mol), of $N^\alpha$-t-butoxycarbonyl glycine and 12.9 g. (0.13 mol) of triethylamine in 500 ml. of ethanol for four days. Nitrogen analysis shows 0.00063 mol per gram.

GENERAL PROCEDURE FOR THE SOLID PHASE SYNTHESIS OF PEPTIDE RESINS

The peptide resin is obtained by attaching an $\alpha$-amino-protected amino acid to a resin (usually a chloromethylated resin which is commercially available from Lab Systems, Inc., San Mateo, California). The peptide system is then constructed by de-protecting the $\alpha$-amino-protected amino acid resin and attaching an $\alpha$-amino-protected amino acid. Repetition of this process produces the peptide resin having the required number and sequence of the desired peptide. The terminal $\alpha$-amino protection is changed by de-protection and attaching the desired carboxylic terminal group. The solid phase synthesis procedure is described by J. M. Stewart "Solid Phase Peptide Synthesis", W. H. Freeman and Co., 1969.

Each cycle of the procedure follows the scheme:
1. De-protection with excess 50% trifluoroacetic acid is dichloromethane.
2. Three washes with dichloromethane.
3. Neutralization of the trifluoroacetic acid salt with an excess of cold 10% triethylamine in dichloromethane.
4. Three washes with dichloromethane.
5. Fifteen to 30 minutes agitation with the $\alpha$-amino-protected amino acid which is present in up to a four-fold molar excess based on the resin nitrogen analysis. However, when a large excess of the $\alpha$-amino-protected amino acid is used it is agitated with the resin for 15 minutes and the excess recovered by draining the solution from the reactor.
6. Addition of dicyclohexylcarbodiimide at least equivalent to the $\alpha$-amino-protected amino acid in Step 5 in dichloromethane followed by agitation for four to twenty hours. In the alternate method, a 3,3-fold excess of dicyclohexylcarbodiimide is used relative to the $\alpha$-amino-protected amino acid resin.
7. Three washes with dichloromethane.

EXAMPLE 2

The methyl ester of Example 1, 1 g., is treated with 60 ml. of methanol saturated with ammonia for twenty-four hours at 25° C. The crude product is isolated by evaporation of the solvent and is precipitated from isopropanol by cooling. The product, $N^\alpha$-t-butoxycarbonyl-L-tryptophyl-O-benzyl-L-seryl-O-benzyl-L-tyrosyl-D-phenylalanyl-L-leucyl-$N^G$-nitro-L-arginyl-L-prolyl-glycinamide, is further purified by chromatography on silica gel with 5% to 15% methanol in benzene; 600 mg.; m.p. 130°–135° C. (decomp); $[\alpha]_D^{23}$ −39° (c 1, dimethylformamide).

EXAMPLE 3

The methyl ester of Example 1, 600 mg., is treated with 10 ml. of ethylamine and 20 ml. of methanol at 25° C. for 18 hours. After evaporation, the crude product is chromatographed on silica gel with 10% benzene in methanol. The fractions selected by thin layer chromatography are evaporated and the residue triturated with petroleum ether giving 150 mg. of $N^\alpha$-t-butoxycarbonyl-L-tryptophyl-O-benzyl-L-seryl-O-benzyl-L-tyrosyl-D-phenylalanyl-L-leucyl-$N^G$-nitro-L-arginyl-L-prolyl-glycine N-ethylamide; m.p. 140°–145° C.

EXAMPLE 4

$N^\alpha$-t-Butoxycarbonyl-L-tryptophyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycine resin, 21.8 g., is treated with methanol, 200 ml. and triethylamine, 20 ml. at room temperature for four days, filtered and the filtrate evaporated. The crude product is chromatographed on silica gel with methanolbenzene (1:4) to give 6.61 g. of $N^\alpha$-t-butoxycarbonyl-L-tryptophyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycine methyl ester, in the form of its hemi-hydrate, m.p. 110°–115° C.

The $N^\alpha$-t-butoxycarbonyl-L-tryptophyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycine resin is obtained by using the general procedure of Example 1, employing 20 g., 0.0126 mol, of $N^\alpha$-t-butoxycarbonyl-glycine resin with 1.) 4.1 g., 0.019 mol, of $N^\alpha$-t-butoxycarbonyl-L-proline and 3.9 g., 0.019 mol, of dicyclohexylcarbodiimide, 2.) 8.5 g., 0.02 mol, of $N^\alpha$-t-butoxycarbonyl-$N^G$-[(4-methylphenyl)sulfonyl]-L-arginine and 3.9 g., 0.019 mol., of dicyclohexylcarbodiimide, 3.) 4.4 g., 0.019 mol, of $N^\alpha$-t-butoxycarbonyl-L-leucine and 3.9 g., 0.019 mol., of dicyclohexylcarbodiimide, 4.) 5.0 g., 0.019 mol., of $N^\alpha$-t-butoxycarbonyl-D-phenylalanine and 3.9 g., 0.019 mol., of dicyclohexylcarbodiimide, 5.) 7.06 g., 0.019 mol., of $N^\alpha$-t-butoxycarbonyl-O-benzyl-L-tyrosine and 3.9 g., 0.019 mol., of dicyclohexylcarbodiimide, 6.) 5.6 g., 0.019 mol., of $N^\alpha$-t-butoxycarbonyl-O-benzyl-L-serine and 3.9 g., 0.019 mol., of dicyclohexylcarbodiimide, 7.) with 26.3 g. of resin obtained in Step 6, 5.2 g., 0.017 mol., of $N^\alpha$-t-butoxycarbonyl-L-tryptophan and 3.5 g., 0.017 mol., of dicyclohexylcarbodiimide.

$N^\alpha$-t-Butoxycarbonyl-glycine resin is obtained by refluxing 100 g., 0.116 mol., of chloromethylated resin, 22.3 g., 0.13 mol., of $N^\alpha$-t-butoxycarbonyl-glycine and 12.9, 0.13 mol., of triethylamine in 500 ml. of absolute alcohol; 104.3 g. Nitrogen analysis shows 0.00063 mol. per gram.

EXAMPLE 5

The methyl ester from Example 4, 1.0 g., 0.00068 mol., is dissolved in 100 ml. of methanol saturated with ammonia and let stand for one day. The product, $N^\alpha$-t-butoxycarbonyl-L-tryptophyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycinamide; 0.9 g., is obtained as a hemi-hydrate after evaporation and chromatography on silica gel using benzene-methanol (80:20); m.p. 119°–125° C.

EXAMPLE 6

The methyl ester from Example 4, 0.3 g., 0.0002 mol, is reacted with 5 ml. of ethylamine in 50 ml. of methanol for two days. The product, $N^\alpha$-t-butoxycarbonyl-L-tryptophyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycine N-ethylamide; 0.21 g., is obtained as a hemi-hydrate after evaporation and chromatography on silica gel using benzene-methanol (80:20); m.p. 115°–120° C.

EXAMPLE 7

$N^\alpha$-t-Butoxycarbonyl-D-leucyl-L-tryptophyl-O-benzyl-L-seryl-O-benzyl-L-tyrosyl-D-alanyl-L-leucyl-$N^G$-nitro-L-arginyl-L-proline resin, 10.5 g., is stirred for two days at 25° C. in 50 ml. of dimethylformamide, 100 ml. of methanol and 20 ml. in triethylamine. The mixture is filtered and the solvents evaporated in vacuo. The residue is recrystallized from isopropanol yielding $N^\alpha$-t-butoxycarbonyl-D-leucyl-L-tryptophyl-O-benzyl-L-seryl-O-benzyl-L-tyrosyl-D-alanyl-L-leucyl-$N^G$-nitro-L-arginyl-L-proline methyl ester; m.p. 130°–135° C.; $[\alpha]_D^{23}$ −29.2° (c 2, DMF).

The above described resin is obtained by reacting 1.7 g. (0.00736 mol.) of $N^\alpha$-t-butoxycarbonyl-D-leucine and 1.5 g. (0.00728 mol.) of dicyclohexylcarbodiimide with 10 g. of $N^\alpha$-t-butoxycarbonyl-L-tryptophyl-O-benzyl-L-seryl-O-benzyl-L-tyrosyl-D-alanyl-L-leucyl-$N^G$-nitro-L-arginyl-L-proline resin in the manner described in Example 1.

The latter resin is obtained by using the general procedure of Example 1, using 70 g. (0.056 mol.) of $N^\alpha$-t-butoxycarbonyl-L-proline resin, 21 g. (0.066 mol.) of $N^\alpha$-t-butoxycarbonyl-$N^G$-nitro-L-arginine, 14 g. (0.068 mol.) of dicyclohexylcarbodiimide; 15.5 g. (0.067 mol.) of $N^\alpha$-t-butoxycarbonyl-L-leucine, 14 g. of dicyclohexylcarbodiimide; 12 g. (0.0635 mol.) of $N^\alpha$-t-butoxycarbonyl-D-alanine, 14 g. of dicyclohexylcarbodiimide; 23.5 g. (0.0632 mol.) of $N^\alpha$-t-butoxycarbonyl-O-benzyl-L-tyrosine, 14 g. of dicyclohexylcarbodiimide; 19 g. (0.0623 mol.) of $N^\alpha$-t-butoxycarbonyl-O-benzyl-L-serine, 14 g. of dicyclohexylcarbodiimide; 19 g. (0.0625 mol.) of $N^\alpha$-t-butoxycarbonyl-L-tryptophan, 14 g. of dicyclohexylcarbodiimide.

The $N^\alpha$-t-butoxycarbonyl-L-proline resin is prepared by refluxing 100 g. (0.116 mol.) of chloromethylated resin with 28 g. (0.130 mol.) of $N^\alpha$-t-butoxycarbonyl-L-proline and 17.4 g. (0.163 mol.) of triethylamine for three days in ethanol. The yield is 112 g.; analysis for nitrogen shows 0.92 mmol. per gram of resin.

EXAMPLE 8

A mixture of 10.5 g. of $N^\alpha$-t-butoxycarbonyl-D-valyl-L-tryptophyl-O-benzyl-L-seryl-O-benzyl-L-tyrosyl-D-alanyl-L-leucyl-$N^G$-nitro-L-arginyl-L-proline resin in 50 ml. of dimethylformamide, 100 ml. of methanol and 20 ml. of triethylamine is stirred for two days at 25° C. The resin is filtered and the filtrate evaporated. The residue is recrystallized from isopropanol to yield $N^\alpha$-t-butoxycarbonyl-D-valyl-L-tryptophyl-O-benzyl-L-seryl-O-benzyl-L-tyrosyl-D-alanyl-L-leucyl-$N^G$-nitro-L-arginyl-L-proline methyl ester; m.p. 140°–145° C.; $[\alpha]_D^{23}$ −30.4° (c 1, DMF).

The above resin is obtained by reacting 1.7 g. (0.0078 mol.) of $N^\alpha$-t-butoxycarbonyl-D-valine and 1.5 g. (0.0073 mol.) of dicyclohexylcarbodiimide with 10 g. of $N^\alpha$-t-butoxycarbonyl-L-tryptophyl-O-benzyl-L-seryl-O-benzyl-L-tyrosyl-D-alanyl-L-leucyl-$N^g$-nitro-L-arginyl-L-proline resin using the general reaction conditions described in Example 1.

EXAMPLE 9

A mixture of 1.8 g. (0.0017 mol) of $N^\alpha$-benzyloxycarbonyl-L-glutaminyl-L-tryptophyl-O-benzyl-L-seryl-O-benzyl-L-tyrosyl-D-phenylalanyl hydrazide and 1 g. (0.027 mol) of hydrogen chloride in 30 ml. of dimethylformamide is cooled to −10° C. and 0.6 ml. of isoamyl nitrite is added. After 30 minutes, the solution is made basic with triethylamine and filtered. The filtrate is treated with 1 g. (0.0022 mol) of L-leucyl-L-arginyl-L-proline N-ethylamide hydrochloride. The solution is kept for three days at 4° C., evaporated and ethyl acetate added to give a solid. The product is converted to the acetate salt by passing a methanol solution through a Dowex 1×2 (acetate form) resin column. The eluate is evaporated, and the product $N^\alpha$-benzyloxycarbonyl-L-glutaminyl-L-tryptophyl-O-benzyl-L-seryl-O-benzyl-L-tyrosyl-D-phenylalanyl-L-leucyl-L-arginyl-L-proline N-ethylamide, purified using a silica gel column with chloroform-methanol-dimethylformamide (70:30:5) for elution; 300 mg., m.p. 160°–165° C.

$N^\alpha$-Benzyloxycarbonyl-L-glutaminyl-L-tryptophyl-O-benzyl-L-seryl-O-benzyl-L-tyrosyl-D-phenylalanyl hydrazide is obtained by treating the methyl ester overnight at 25° C. with an excess of hydrazine hydrate in dimethylformamide solution. The hydrazide is precipitated by the addition of ether to the dimethylformamide solution and the product is used without further purification.

$N^\alpha$-Benzyloxycarbonyl-L-glutaminyl-L-tryptophyl-O-benzyl-L-seryl-O-benzyl-L-tyrosyl-D-phenylalanine methyl ester is obtained by treatment of $N^\alpha$-benzyloxycarbonyl-L-glutaminyl-L-tryptophyl-O-benzyl-L-seryl-O-benzyl-L-tyrosyl-D-phenylalanyl resin, 17 g., with 200 ml. of methanol and 20 ml. of triethylamine for two days at 25° C. The resin is filtered, the filtrate evaporated and the residue triturated with isopropanol to give 2.8 g. of solid; m.p. 220°–223° C.

The above resin is prepared by the general procedure of Example 1, using 13 g. (0.0082 mol.) of $N^\alpha$-t-butoxycarbonyl-D-phenylalanine resin; 5.2 g. (0.014 mol.) of $N^\alpha$-t-butoxycarbonyl-O-benzyl-L-tyrosine, 2.88 of dicyclohexylcarbodiimide; 4.5 g. (0.0148 mol.) of $N^\alpha$-t-butoxycarbonyl-O-benzyl-L-serine, 3 g. (0.0148 mol.) of dicyclohexylcarbodiimide; 4 g. (0.013 mol.) of $N^\alpha$-t-butoxycarbonyl-L-tryptophan, 2.7 g. (0.013 mol.) of dicyclohexylcarbodiimide; 8 g. (0.020 mol.) of $N^\alpha$-benzyloxycarbonyl-L-glutamine p-nitrophenyl ester.

$N^\alpha$-t-Butoxycarbonyl-D-phenylalanine resin is obtained by refluxing 40 g. (0.046 mol.) of chloromethylated resin, 14 g. (0.0528 mol.) of $N^\alpha$-t-butoxycarbonyl-D-phenylalanine and 5.2 g. (0.052 mol) of triethylamine in 300 ml. of ethanol for three days. The resin is filtered, washed with ethanol and dried, 46 g.

To a solution of 1.8 g. of $N^\alpha$-benzyloxycarbonyl-L-leucyl-L-arginyl-L-prolyl-N-ethylamide hydrochloride in 100 ml. of methanol is added 400 mg. of 20% palladium on carbon and the mixture is stirred under a hydrogen atmosphere for four hours. Disappearance of the starting material is determined by thin layer chromatography of samples of the solution. The catalyst is removed by filtration and the filtrate is evaporated to dryness. The product, L-leucyl-L-arginyl-L-prolyl-N-ethylamide hydrochloride, is used without further purification.

A solution of 18.6 g. of L-arginyl-L-prolyl-N-ethylamide hydrochloride and 7.2 g. of $N^\alpha$-benzyloxycarbonyl-L-leucine p-nitrophenylester in 30 ml. of dimethylformamide is allowed to stand for four days, warmed to 50° C. for a half hour and evaporated at reduced pressure and 40° C. to yield an oil. A solid product is obtained by chromatography over silica gel, eluting with chloroform with increasing percent of methanol. Fraction selection is made on the basis of analytical thin layer chromatography and the product, $N^\alpha$-benzyloxycarbonyl-L-leucyl-L-arginyl-L-prolyl-N-ethylamide hydrochloride, obtained solid by precipitating from methanol with ethyl acetate and then by dropping a methanol solution into ethyl ether. The solid is dried at 40° C. and reduced pressure; $[\alpha]_D^{25}$ −68.4° (c 1, methanol).

A solution of 8.7 g. of $N^\alpha$-benzyloxycarbonyl-L-arginyl-L-prolyl-N-ethylamide hydrochloride in 100 ml. of methanol is stirred with 500 mg. of 20% palladium on carbon under one inch water pressure of hydrogen for three hours. The catalyst is removed by filtration and the filtrate evaporated under reduced pressure and at 35°–40° C. The residual foam, L-arginyl-L-prolyl-N-ethylamide, hydrochloride, is used without further purification.

To a cold solution of 9.7 g. ethylamine in 50 ml. of methanol is added 2 g. of $N^\alpha$-benzyloxycarbonyl-L-arginyl-L-proline, methyl ester, hydrochloride. The reaction is let stand in a sealed pressure bottle at room temperature and then warmed occasionally to 40°–45° C. during eight days. It is then evaporated to a small volume under reduced pressure. The residual solution is dropped into stirred ethyl ether to precipitate a somewhat sticky white white solid, $N^\alpha$-benzyloxycarbonyl-L-arginyl-L-prolyl-N-ethylamide, hydrochloride, which is dried under reduced pressure; $[\alpha]_D^{25}$ −53° C. (c 1.02, methanol)

We claim:

1. A octapeptide having the name $N^\alpha$-t-butoxycarbonyl-L-tryptophyl-O-benzyl-L-seryl-O-benzyl-L-tyrosyl-D-phenylalanyl-L-leucyl-$N^G$-nitro-L-arginyl-L-prolylglycine methyl ester.

2. A octapeptide having the name $N^\alpha$-t-butoxycarbonyl-L-tryptophyl-O-benzyl-L-seryl-O-benzyl-L-tyrosyl-D-phenylalanyl-L-leucyl-$N^G$-nitro-L-arginyl-L-prolylglycinamide.

3. A octapeptide having the name $N^\alpha$-t-butoxycarbonyl-L-tryptophyl-O-benzyl-L-seryl-O-benzyl-L-tyrosyl-D-phenylalanyl-L-leucyl-$N^G$-nitro-L-arginyl-L-prolylglycine N-ethylamide.

4. A compound having the name $N^\alpha$-t-butoxycarbonyl-L-tryptophyl-O-benzyl-L-seryl-O-benzyl-L-tyrosyl-D-phenylalanyl-L-leucyl-$N^G$-(4-methylphenyl)sulfonyl-L-arginyl-L-prolylglycine methyl ester.

5. A compound having the name $N^\alpha$-t-butoxycarbonyl-L-tryptophyl-O-benzyl-L-seryl-O-benzyl-L-tyrosyl-D-phenylalanyl-L-leucyl-$N^G$-(4-methylphenyl)sulfonyl-L-arginyl-L-prolylglycine amide.

6. A compound having the name $N^\alpha$-t-butoxycarbonyl-L-tryptophyl-O-benzyl-L-seryl-O-benzyl-L-tyrosyl-D-phenylalanyl-L-leucyl-$N^G$-(4-methylphenyl)sulfonyl-L-arginyl-L-prolyl-glycine-N-ethylamide.

7. A compound having the name $N^\alpha$-t-butoxycarbonyl-D-leucyl-L-tryptophyl-O-benzyl-L-seryl-O-benzyl-L-tyrosyl-D-alanyl-L-leucyl-$N^G$-nitro-L-arginyl-L-proline methyl ester.

8. A compound having the name $N^\alpha$-t-butoxycarbonyl-D-valyl-L-tryptophyl-O-benzyl-L-seryl-O-benzyl-L-tyrosyl-D-alanyl-L-leucyl-$N^G$-nitro-L-arginyl-L-proline methyl ester.

9. A compound having the name $N^\alpha$-benzyloxycarbonyl-L-glutaminyl-L-tryptophyl-O-benzyl-L-seryl-O-benzyl-L-tyrosyl-D-phenylalanyl-L-leucyl-L-arginyl-L-proline-N-ethylamide and acid addition salts thereof.

10. A compound having the name $N^\alpha$-benzyloxycarbonyl-L-glutaminyl-L-tryptophyl-O-benzyl-L-seryl-O-benzyl-L-tyrosyl-D-alanyl-L-leucyl-L-arginyl-L-proline-N-ethylamide and acid addition salts thereof.

11. A compound having the name $N^\alpha$-t-butoxycarbonyl-D-glutaminyl-L-tryptophyl-O-benzyl-L-seryl-O-benzyl-L-tyrosyl-D-alanyl-L-leucyl-$N^G$-nitro-L-arginyl-L-proline methyl ester.

* * * * *